United States Patent [19]

Hamaguri

[11] Patent Number: 4,694,833
[45] Date of Patent: * Sep. 22, 1987

[54] NONINVASIVE DEVICE FOR PHOTOELECTRICALLY MEASURING THE PROPERTY OF ARTERIAL BLOOD

[75] Inventor: Kenji Hamaguri, Sakai, Japan

[73] Assignee: Minolta Camera Kabushiki Kaisha, Osaka, Japan

[*] Notice: The portion of the term of this patent subsequent to May 6, 2003 has been disclaimed.

[21] Appl. No.: 839,433

[22] Filed: Mar. 13, 1986

Related U.S. Application Data

[62] Division of Ser. No. 467,431, Feb. 17, 1983, Pat. No. 4,586,513.

[30] Foreign Application Priority Data

Feb. 19, 1982 [JP] Japan .................................. 57-26639

[51] Int. Cl.[4] .............................. A61B 5/00; A61B 6/00
[52] U.S. Cl. ..................................... 128/633; 128/666; 356/41
[58] Field of Search ............... 128/633, 634, 665, 666; 356/41

[56] References Cited

U.S. PATENT DOCUMENTS

| | | | |
|---|---|---|---|
| 3,638,640 | 2/1972 | Shaw | 128/2 R |
| 3,998,550 | 12/1976 | Konishi et al. | 356/39 |
| 4,086,915 | 5/1978 | Kofsky et al. | 128/2 L |
| 4,114,604 | 9/1978 | Shaw et al. | 128/634 |
| 4,167,331 | 9/1979 | Nielsen | 356/39 |
| 4,453,218 | 6/1984 | Sperinde et al. | 128/634 X |
| 4,586,513 | 5/1986 | Hamaguri | 128/633 |
| 4,623,248 | 11/1986 | Sperinde | 128/634 |

*Primary Examiner*—Kyle L. Howell
*Assistant Examiner*—John C. Hanley
*Attorney, Agent, or Firm*—Price, Gess & Ubell

[57] ABSTRACT

A noninvasive device for photoelectrically measuring a property of arterial blood is provided. Light that contacts living tissue with arterial blood is converted into a pair of electrical signals. The electrical signals are processed to provide information of the amplitude of the measured signals and are further processed to produce a final output signal that is substantially a square function of a ratio between the electrical signals representative of the amplitudes.

20 Claims, 13 Drawing Figures

NONINVASIVE DEVICE FOR PHOTOELECTRICALLY MEASURING THE PROPERTY OF ARTERIAL BLOOD

This is a divisional of application Ser. No. 467,431, filed Feb. 17, 1983, now U.S. Pat. No. 4,586,513.

BACKGROUND OF THE INVENTION

1. Field of the Invention

The present invention relates to a noninvasive device for photoelectrically measuring a property of arterial blood, such as an oximeter or a densitometer for measurement of a pigment in blood.

2. Description of the Prior Art

The behavior of light in materials has been a topic of study in various theoretical works such as disclosed in "New Contributions to the Optics of Intensely Light-Scattering Materials. Part 1," by Paul Kubelka, *Journal of the Optical Society of America,* Volume 38, No. 5, May, 1983; "Optical Transmission and Reflection by Blood," by R. J. Zdrojkowski and N. R. Pisharoty, *IEEE Transactions on Bio-Medical Engineering,* Vol. BME-17, No. 2, April, 1970, and "Optical Diffusion in Blood," by Curtis C. Jhonson, *IEEE Transactions on Bio-Medical Engineering,* Vol. BME-17, No. 2, April, 1970.

On the other hand, various practical devices or methods for measuring blood property have been disclosed in the patent literature such as U.S. Pat. Nos. 3,368,640, 3,998,550 and 4,086,915, and Japanese Patent Publication No. 53-26437.

In the specific field of the medical-optical art noninvasive measurements relating to the amount of a pigment in the blood, such as hemoglobin, hemoglobin oxide, bilirubin or an artificially injected pigment, have generally taken the following form. The oximeter usually comprises means for providing a source light; means for photoelectrically measuring the intensity of the source light after contact with a living tissue containing the arterial blood at a first wavelength, at which the light absorption coefficients for hemoglobin and hemoglobin oxide are equal, and a second wavelength, at which the two light absorption coefficients greatly differ from each other, to produce a pair of electric signals, respectively, the signals each include an alternating-current (AC) component and a direct-current (DC) component; means for calculating information representative of the amplitude of the alternating-current component relative to the direct-current component with respect to the first and second wavelengths to produce a first and second calculated output, respectively; means for presenting a final output indicative of the oxygen saturation, and means for relating the final output with the first and second calculated outputs so that the final output is a linear function of a ratio between the first and second calculating outputs.

However, clinical experiences have recently reported that an oximeter of the above type was apt to show some aberration or error of measurement in the relatively lower oxygen saturation range although the measurements are quite accurate in the higher oxygen saturation range. Thus there is still a need in the prior art to provide improved electro-optical measuring devices for medical use.

SUMMARY OF THE INVENTION

An object of the present invention is to provide a non-invasive device for photoelectrically measuring a property of arterial blood with high accuracy throughout a wide measurement range.

Another object of the present invention is to provide a novel oximeter capable of measuring the oxygen saturation with an improved accuracy throughout a wide oxygen saturation range.

According to the present invention the relation of the final output, such as the oxygen saturation or a density of the pigment in the blood, with the above-mentioned first and second calculating outputs is determined so that the final output is a square function of a ratio between the first and second calculating outputs, or a joint combination of a plurality of linear functions which correspond to an approximation of the square function.

The objects and features of the present invention which are believed to be novel are set forth with particularity in the appended claims. The present invention, both as to its organization and manner of operation, together with further objects and advantages thereof, may best be understood by reference to the following description, taken in connection with the accompanying drawings.

DESCRIPTION OF THE PREFERRED EMBODIMENTS

The following description is provided to enable any person skilled in the electro-optical art to make and use the present invention and sets forth the best modes contemplated by the inventor of carrying out his invention. Various modifications, however, will remain apparent to those skilled in the art, since the generic principles of the present invention have been defined herein specifically to provide a noninvasive device for photoelectrically measuring a property of blood.

Figure 1:
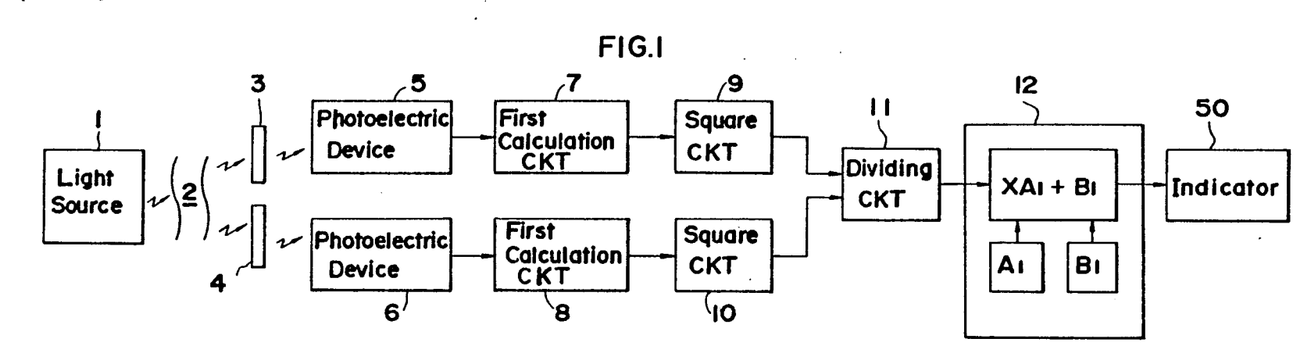
FIG. 1 represents a block diagram of a first embodiment of the present invention.
Figures 2, 3, 4, 5:
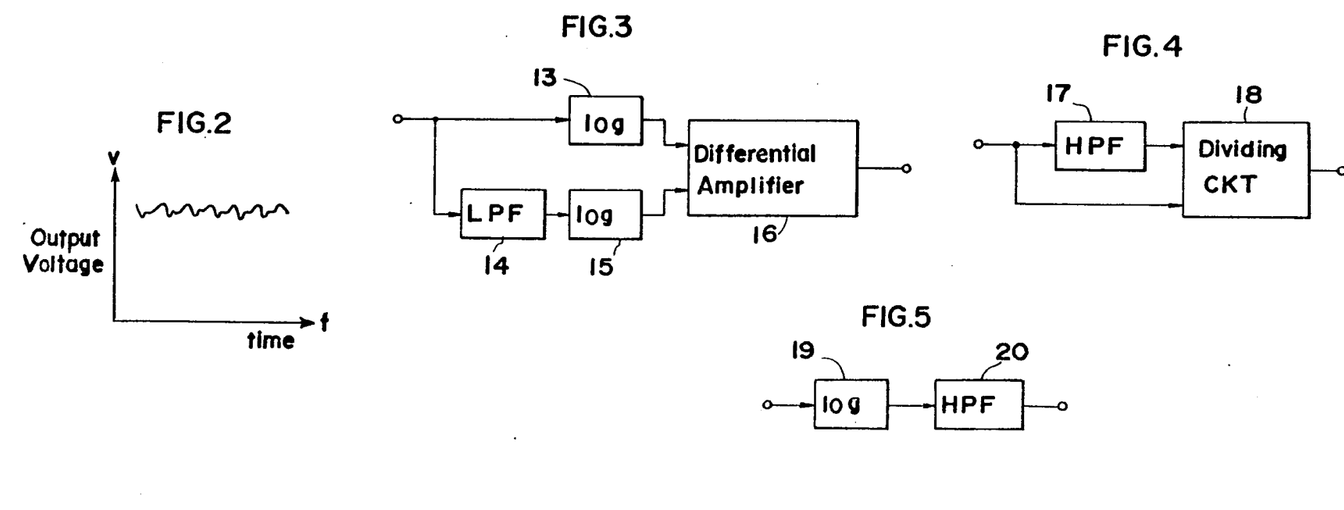
FIG. 2 represents graphic plots of output voltages of the photoelectric device of FIG. 1.
FIG. 3 represents a block diagram of a first type of the first calculation circuit in FIG. 1.
FIG. 4 represents a block diagram of a second type of the first calculation circuit in FIG. 1.
FIG. 5 represents a block diagram of a third type of the first calculation circuit in FIG. 1.

FIG. 1 represents a block diagram of a first embodiment of the present invention in the form of an oximeter, in which a source light having a wide wavelength band emerges from a light source 1 to enter interference filters 3 and 4, respectively, by way of transmission through the living tissue 2 being monitored. The peak of transmission of interference filter 3 is at a wavelength, $\lambda_1$ at which the light absorption coefficient for the hemoglobin is equal to that for the hemoglobin oxide, while the peak of transmission of interference filter 4 is at a wavelength, $\lambda_2$ wherin the two light absorption coefficients are greatly different from each other. Thus, photoelectric devices 5 and 6 are responsive to the intensities of light at wavelengths, $\lambda_1$ and $\lambda_2$, respectively. The changes depending on the lapse of time in output voltages of photoelectric devices 5 and 6 are shown in FIG. 2, wherein an alternating-current (AC) compound is added to a direct-current (DC) component since the light transmitted through living tissue is generally absorbed by muscle, bone, venous blood and arterial blood, and the quantity of arterial blood periodically changes in response to the pulsation of the heart in contrast to other unchanged factors.

A pair of first calculation circuits 7 and 8 each calculate information representative of the amplitude of the alternating-current component relative to the direct-current component with respect to wavelengths, $\lambda_1$ and $\lambda_2$, respectively. The pair of outputs, which are derived from the first calculation circuits 7 and 8, are squared by a pair of square circuits 9 and 10, respectively. Dividing circuit 11 is for obtaining the ratio between the outputs from the pair of square circuits 9 and 10. The output, X of dividing circuit 11, which corresponds to the square of the ratio between the outputs of the pair of first calculation circuits 7 and 8, is transmitted to a linear function circuit 12 to be multiplied by a first constant, $A_1$ and added to a second constant, $B_1$. The results of the calculation by the linear function circuit 12 is representative of the oxygen saturation of blood and can be displayed by some indicator 50 such as a meter or a digital display circuit.

In more detail, according to the present invention, the output voltages, $E_1$ and $E_2$ of the pair of photoelectric devices 5 and 6 are defined as follows, respectively:

$$E_1 = K_1 I_{01} F_{T1} D_1 e^{-g_1 \sqrt{\beta_1}\ (d+\Delta d)} \tag{1}$$

$$E_2 = K_2 I_{02} F_{T2} D_2 e^{-g_2 \sqrt{\beta_2}\ (d+\Delta d)} \tag{2}$$

Wherein: $K_1$ and $K_2$ represent a pair of constants determined by photosensitive elements in the photoelectric devices 5 and 6, respectively; $I_{01}$ and $I_{02}$ represent the intensities of source light at wavelengths, $\lambda_1$ and $\lambda_2$, respectively; $F_{T1}$ and $F_{T2}$ represent the light absorption coefficients of materials other than the arterial blood at wavelengths, $\lambda_1$ and $\lambda_2$, respectively; $D_1$ and $D_2$ represents a pair of constants depending on the scattering coefficient and the absorption coefficient of the arterial blood at wavelengths, $\lambda_1$ and $\lambda_2$, respectively; $g_1$ and $g_2$ represent a pair of constants depending on the scattering coefficient of the arterial blood at wavelengths $\lambda_1$ and $\lambda_2$ and the total density of the hemoglobin and the hemoglobin oxide, respectively; $\beta_1$ and $\beta_2$ represent the light absorption coefficients of the arterial blood at wavelengths, $\lambda_1$ and $\lambda_2$; d represents an average thickness of the arterial blood; and $\Delta d$ represents the change depending on the lapse of time in the thickness of the arterial blood.

In determining the above equations (1) and (2), the present invention regards the light measured by way of transmission through the living tissue as determined under the conditions that:

(i) the influence of scattering by the arterial blood is not negligible;

(ii) the optical path in the living tissue is sufficiently long; and (iii) the scattering coefficient is sufficiently great relative to the absorption coefficient.

The pair of first calculation circuits 7 and 8 each may be practically designed in accordance with any one of FIGS. 3, 4 and 5. Specifically, the circuit in FIG. 3 comprises a first logarithmic conversion circuit 13 to obtain a logarithm of the output from the photoelectric device 5 or 6, a low-pass filter 14, a second logarithmic conversion circuit 15 to obtain a logarithm of the direct-current component of the output from the photoelectric device 5 or 6, and a differential amplifier 16 to subtract the output of circuit 15 from the output of circuit 13, for calculating a logarithm of a ratio of the whole output of photoelectric device 5 or 6 to the direct-current component thereof. On the other hand, the circuit in FIG. 4 comprises a high-pass filter 17 to obtain the alternating-current component of the output from photoelectric device 5 or 6, and a dividing circuit 18, for calculating a ratio of the alternating-current component of the output of photoelectric device 5 or 6 to the whole output thereof. Further, the circuit in FIG. 5 comprises a logarithmic conversion circuit 19 to obtain the logarithm of the output of photoelectric device 5 or 6 and a high-pass filter 20 to obtain the alternating-current component of the output of circuit 19.

In designing the oximeter, the pair of first calculating circuits 7 and 8 should adopt the same type of circuit, although the type may be selectable among FIGS. 3 to 5. Any one of the circuits in FIGS. 3 to 5 is substantially capable of calculating information representative of the relative amplitude of the alternating-current component of the output of photoelectric device 5 or 6, although the degree of approximation is individually different.

Thus, the output voltages, $E_3$ and $E_4$ of the pair of first calculating circuits 7 and 8 in FIG. 1 are given in accordance with the following equations, respectively:

$$E_3 = g_1 \sqrt{\beta_1}\ \Delta d \tag{3}$$

$$E_4 = g_2 \sqrt{\beta_2}\ \Delta d \tag{4}$$

Figure 6:
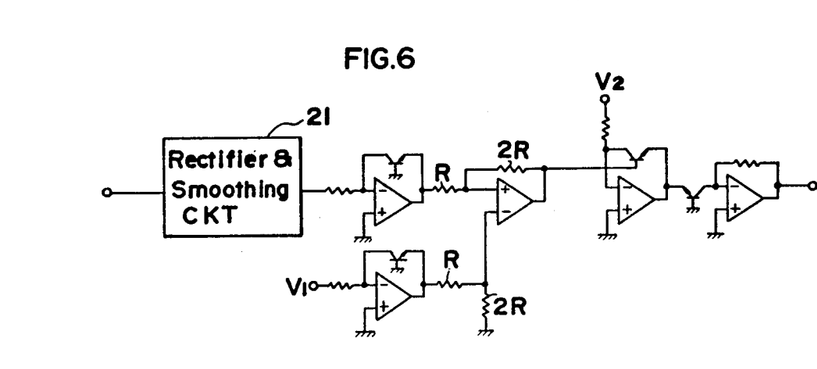
FIG. 6 represents a circuit diagram of the details of the square circuit in FIG. 1.

FIG. 6 represents an example of a detailed circuit applicable for square circuits 9 and 10, and its function is self-evident to a person skilled in the optical electrical art without any further explanation. However, it is pointed out that block 21 represents a rectifier and smoothing circuit connected to the output of the first calculation circuit 7 or 8.

The output voltages, $E_5$ and $E_6$ of the pair of square circuits 9 and 10 in FIG. 1 is as follows:

$$E_5 = (g_1 \Delta d)^2 \beta_1 \tag{5}$$

$$E_6 = (g_2 \Delta d)^2 \beta_1 \qquad (6)$$

Further, the output voltage, $E_7$ of the dividing circuit 11 is as follows:

$$E_7 = \left(\frac{g_2}{g_1}\right)^2 \frac{\beta_2}{\beta_1} = \left(\frac{E_4}{E_3}\right)^2 \qquad (7)$$

Here, it should be noted that the light absorption coefficients, $\beta_1$ and $\beta_2$ are generally defined by the following equations:

$$\beta_1 = C\{S[a_1(HbO_2) - a_1(Hb)] + a_1(Hb)\} \qquad (8)$$

$$\beta_2 = C\{S[a_2(HbO_2) - a_2(Hb)] + a_2(Hb)\} \qquad (9)$$

wherein: $a_1(HbO_2)$ and $a_2(HbO_2)$ represent the light absorption coefficients of hemoglobin oxide, $HbO_2$ at wavelengths, $\lambda_1$ and $\lambda_2$, respectively; $a_1(Hb)$ and $a_2(Hb)$ represent the light absorption coefficients of hemoglobin, $Hb$ at wavelengths, $\lambda_1$ and $\lambda_2$; C represents the total density of the hemoglobin and the hemoglobin oxide in the arterial blood; and S represents the oxygen saturation in the arterial blood.

Equation (8) is simplified as follows since $a_1(HbO_2) = a_1(Hb)$ at wavelength $\lambda_1$:

$$\beta_1 = Ca_1(Hb) \qquad (10)$$

From equations (7), (9) and (10), the following equation (11) results:

$$\left(\frac{E_4}{E_3}\right)^2 = \left(\frac{g_2}{g_1}\right)^2 \frac{S[a_2(HbO_2) - a_2(Hb)] + a_2(Hb)}{a_1(Hb)} \qquad (11)$$

Therefore, $$S = \frac{a_1(Hb)}{a_2(HbO_2) - a_2(Hb)} \left(\frac{g_1}{g_2}\right)^2 \left(\frac{E_4}{E_3}\right)^2 - \frac{a_2(Hb)}{a_2(HbO_2) - a_2(Hb)} \qquad (12)$$

The constants $A_1$ and $B_1$ are defined by the following equations:

$$A_1 = \frac{a_1(Hb)}{a_2(HbO_2) - a_2(Hb)} \left(\frac{g_1}{g_2}\right)^2 \qquad (13)$$

$$B_1 = -\frac{a_2(Hb)}{a_2(HbO_2) - a_2(Hb)} \qquad (14)$$

The above equation (12) can be further summarized as follows:

$$S = A_1 \left(\frac{E_4}{E_3}\right)^2 + B_1 \qquad (15)$$

Figure 7:
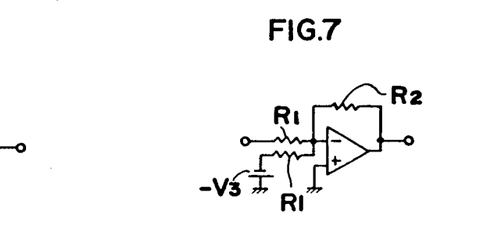
FIG. 7 represents a circuit diagram of the details of the linear function circuit in FIG. 1.

This means that the oxygen saturation S is calculated as a linear function of $(E_4/E_3)^2$, which represents a square of the ratio between the outputs of the pair of first calculation circuits 7 and 8. Linear function circuit 12 performs the calculation in accordance with the linear function defined by equation (12). FIG. 7 represents an example of a detailed circuit applicable to a linear function circuit and its function will be self-evident with no additional explanation. However, it should be noted that the circuit constants $R_1$ to $R_3$ and $V_3$ have to fulfill the following equations:

$$-\frac{R_2}{R_1} = A_1$$

$$-\frac{R_2}{R_1} \cdot (-V_3) = B_1$$

The values for $A_1$ and $B_1$ can be determined in accordance with equations (13) and (14), respectively.

Figure 8:
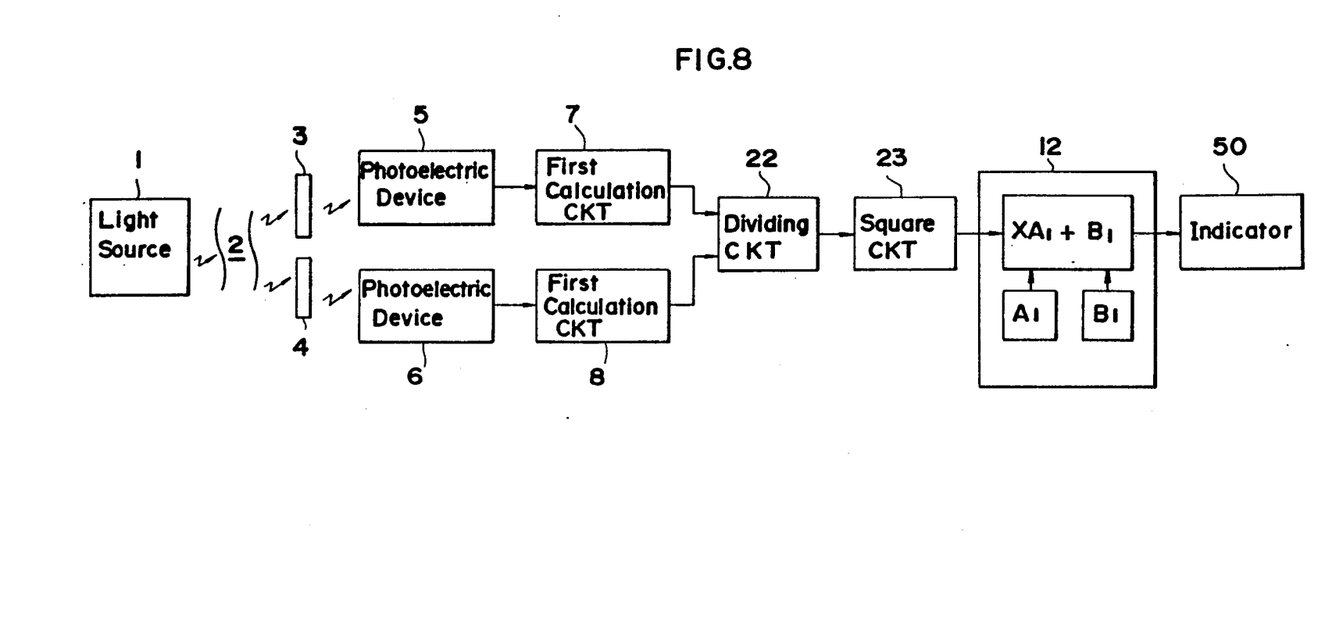
FIG. 8 represents a block diagram of a second embodiment of the present invention.

FIG. 8 represents a second embodiment of the present invention, in which the same elements as those in FIG. 1 are indicated by the same symbols and explanations thereof are accordingly omitted.

In summary, the same embodiment in FIG. 8 is substantially identical with the first embodiment in FIG. 1 except that the outputs of the pair of first calculation circuits 7 and 8 are subjected to division in dividing circuit 22 and, in turn, squared by a single square circuit 23, in place of each being squared by a pair of square circuits 9 and 10 prior to being divided by dividing circuit 11 in FIG. 1. The circuit in FIG. 6 is also applicable as square circuit 23 in FIG. 8. The output voltage, $E_8$ of dividing circuit 22 is given as follows:

$$E_8 = \frac{g_2}{g_1} \sqrt{\frac{\beta_2}{\beta_1}}$$

Further, the output voltage, $E_9$ of square circuit 23 is given as follows:

$$E_9 = \left(\frac{g_2}{g_1}\right)^2 \frac{\beta_2}{\beta_1} = \left(\frac{E_4}{E_3}\right)^2,$$

which is identical with equation (7).

Figure 9:
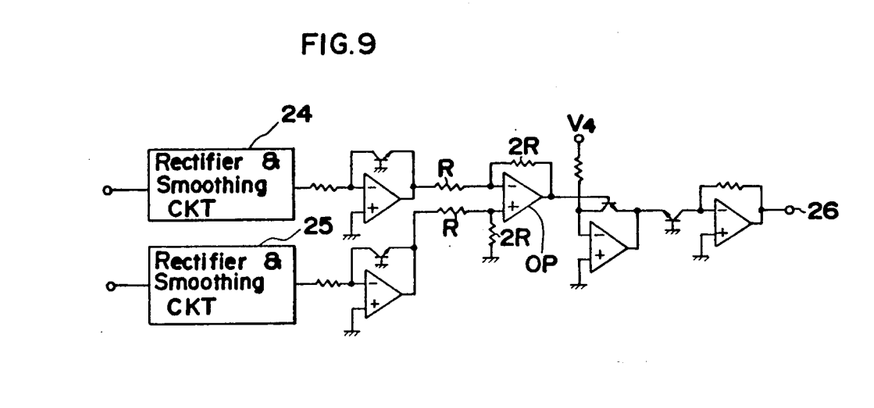
FIG. 9 represents a circuit diagram showing a modification of the square circuit and dividing circuit in either FIG. 1 or FIG. 8.

FIG. 9 provides a modification of the embodiments in FIGS. 1 and 8. Namely, the circuits 9, 10 and 11 in FIG. 1 or the equivalent circuits 22 and 23 in FIG. 8 can be alternatively constructed as a composite circuit in FIG. 9 capable of both the squaring and dividing functions, and its operation will be self-evident without additional explanation except that the rectifier and smoothing circuits 24 and 25 are connected to the pair of first calculation circuits 7 and 8, respectively, and that the gain of the differential amplifier OP in FIG. 9 should be set at twice the value for the purpose of obtaining the following output at terminal 26:

$$\left(\frac{g_2}{g_1}\right)^2 \frac{\beta_2}{\beta_1}$$

Figure 10:
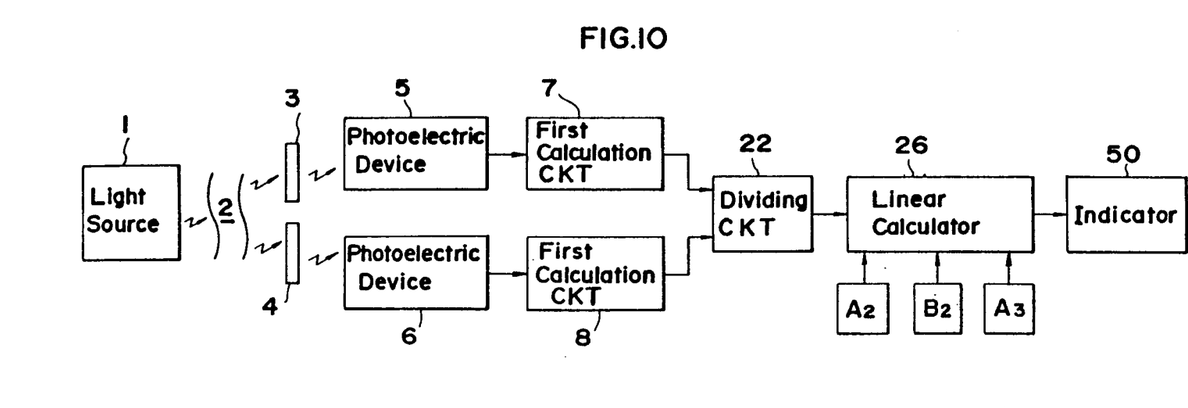
FIG. 10 represents a block diagram of a third embodiment of the present invention.

FIG. 10 represents a third embodiment of the present invention, in which the same elements as those in FIG. 8 are indicated by the same symbols to avoid any redundant explanation. The third embodiment is designed in accordance with the findings that equation (15), which is a square function of $E_4/E_3$, can be approximately substituted by a joint combination of the following linear functions of $E_4/E_3$, provided that the oxygen saturation is greater than 50 percent:

(i) when $E_4/E_3 < M$, $$S = A_2 \cdot \frac{E_4}{E_3} - B_2 \tag{16}$$

(ii) when $E_4/E_3 \geq M$, $$S = A_3 \left( \frac{E_4}{E_3} - M \right) + A_2 M + B_2 \tag{17}$$

wherein, $A_2$, $B_2$, $B_3$ and M are given constants, respectively. In FIG. 10, linear function circuit 26 is capable of determining whether or not $E_4/E_3$ is greater than M in addition to calculating the oxygen saturation S in accordance with equation (16) or (17) selected in response to such a determination.

Figure 11:
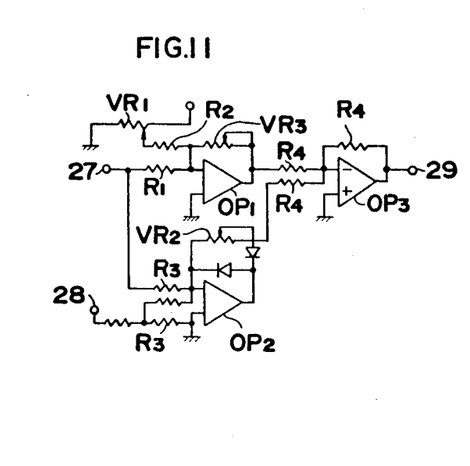
FIG. 11 represents a circuit diagram of a detail of the linear function circuit in FIG. 10.

FIG. 11 represents an example of a circuit applicable to such a linear function circuit 26. In FIG. 11, the output, $E_4/E_3$ of dividing circuit 22 is transmitted to terminal 27 as a positive voltage. At terminal 28, a negative voltage $V_5$, which fulfills $M = -V_5$, is transmitted.

When $E_4/E_3 < -V_5$, the output of differential amplifier $OP_2$ is zero to allow only the output of differential amplifier $OP_1$ to be transmitted to differential amplifier $OP_3$. The output voltage of differential amplifier $OP_1$ is designed to be equal to the following value for the input, $E_4/E_3$ by means of adjusting the variable resistors $VR_1$ and $VR_2$:

$$-\left( A_2 \cdot \frac{E_4}{E_3} + B_2 \right) \tag{18}$$

Thus, the output voltage of differential amplifier $OP_3$ connected to terminal 28 is as follows when $E_4/E_3 < -V_5$:

$$A_2 \cdot \frac{E_4}{E_3} + B_2 \tag{19}$$

which is identical with equation (16).

On the other hand, when $E_4/E_3 \geq -V_5$, the output voltage or differential amplifier $OP_2$ is as follows, provided that $R_5$ represents the resistance of variable resistor $VR_2$:

$$-\frac{R_5}{R_3} \left( \frac{E_4}{E_3} + V_5 \right) \tag{20}$$

The output voltage at terminal 29 in this case is as follows since the voltages of above values (18) and (20) are both transmitted to differential amplifier $OP_3$:

$$\left( A_2 + \frac{R_5}{R_3} \right) \frac{E_4}{E_3} + B_2 + \frac{R_5}{R_3} V_5 =$$

$$A_3 \left( \frac{E_4}{E_3} - M \right) + A_2 M + B_2,$$

which is identical with equation (17) provided that:

$$A_2 + \frac{R_5}{R_3} = A_3$$

Since the third embodiment is only an example of approximately substituting the square function (15) by a combination of a plurality of linear functions, it is needless to say that any other approximation by means of utilizing another combination of a plurality of linear functions, e.g., three or more linear functions, can be possible within the scope of the present invention.

Figure 12:
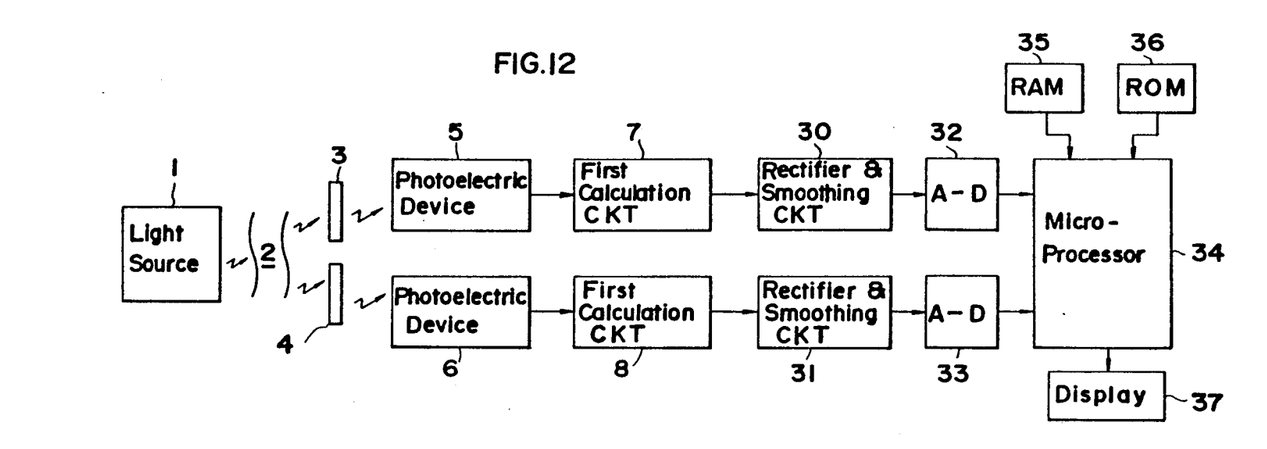
FIG. 12 represents a block diagram of a fourth embodiment of the present invention.

FIG. 12 represents a fourth embodiment of the present invention, in which the analog outputs $E_3$ and $E_4$ of the pair of first calculation circuits 7 and 8 are converted into digital signals $P_1$ and $P_2$ by means of a pair of rectifiers and smoothing circuits 30 and 31 and A-D converters 32 and 33, respectively. The digital signals $P_1$ and $P_2$ can be processed by microprocessor 34 with random access memory (RAM) 35 and read only memory (ROM) 36 to indicate the oxygen saturation by means of a digital display 37.

For example, microprocessor 34 is programmed to carry out the following calculation, as in the first and second embodiments:

$$S = A_1 \left( \frac{P_2}{P_1} \right)^2 + B_1 \tag{21}$$

Or, alternatively, microprocessor 34 is programmed to discriminate between the following cases (i) and (ii) to select one of them, and carry out the calculation in accordance with the selected case, as in the third embodiment:

(i) when $P_2/P_1 < M$, $$S = A_2 \cdot \frac{P_2}{P_1} + B_2$$

(ii) when $P_2/P_1 \geq M$, $$S = A_3 \left( \frac{P_2}{P_1} - M \right) + A_2 M + B_2$$

The above constants $A_1$, $B_1$, $A_2$, $B_2$, $A_3$ and M may be stored in RAM 35 or ROM 36, or alternatively be inputted by means of a combination of a plurality of switches representative of a digital code.

Another example of the function of microprocessor 34, RAM 35 and ROM 36 in the fourth embodiment in FIG. 12 is as follows. Namely, various oxygen saturation values, $S_0$, $S_1$, $S_2$, ..., $S_i$, ..., $S_{n-1}$ and $S_n$ have been previously calculated in accordance with equation (21) for various possible values $(P_2/P_1)_0$, $(P_2P_1)_1$, $(P_2P_1)_2$, ..., $(P_2P_1)_i$, ..., $(P_2/P_1)_{n-1}$ and $(P_2/P_1)_n$ and stored in ROM 36 at addresses K, K+1, K+2, ..., K+i, ... K+n, respectively. And $(P_2/P_1)_i$ fulfilling the following condition is searched with respect to the actually obtained ratio $P_2/P_1$:

$$(P_2/P_1)_i \leq P_2/P_1 < (P_2/P_1)_{i+1}$$

to determine address K+i at which the desired oxygen saturation $S_i$ is stored. The oxygen saturation $S_i$ is read out from ROM 36 and displayed at digital display 37.

Strictly speaking, such an oxygen saturation $S_i$ is not accurately equal to the oxygen saturation S which would be directly calculated in accordance with equation (21). However, $S_i$ is practically regarded as S if the number, n is sufficiently great.

Or, if n is desired to be not so great, than a further modification is possible such that S is calculated by microprocessor 34 in accordance with a suitable interpolation such as:

$$S = S_i + (S_{i+1} - S_i) \frac{P_2/P_1 - (P_2/P_1)_i}{(P_2/P_1)_{i+1} - (P_2/P_1)_i}$$

Although FIG. 12 discloses that the device includes two A-D converters 32 and 33, such a modification is possible that only one A-D converter is alternatively utilized which is connected to both circuits 30 and 31 by way of a suitable multiplexer controlled through microprocessor 34.

Figure 13:
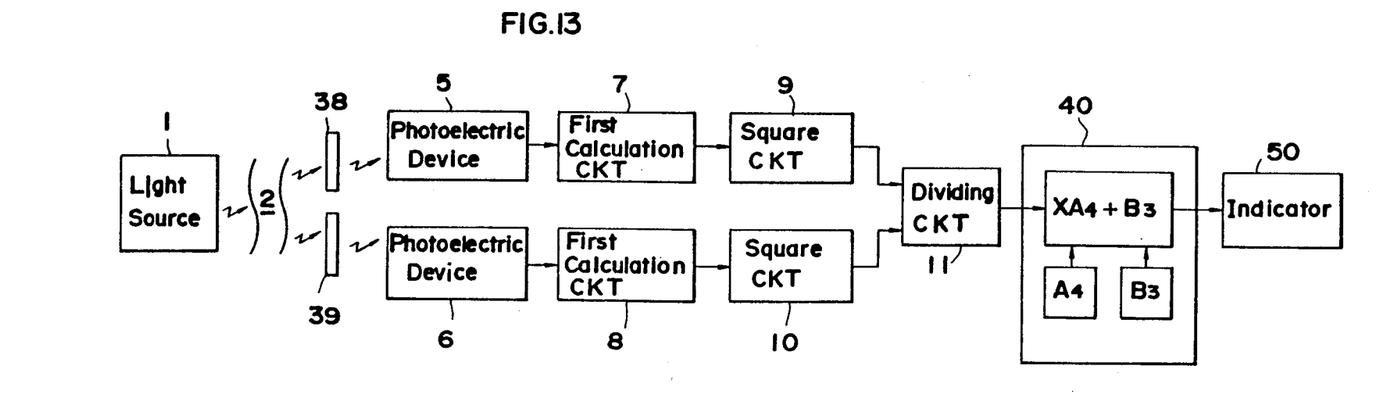
FIG. 13 represents a block diagram of a fifth embodiment of the present invention.

FIG. 13 represents a fifth embodiment of the present invention constructed as a densitometer for a desired pigment, such as bilirubin or an artificially injected pigment, in the arterial blood in contrast to the foregoing embodiments which are constructed as an oximeter. In FIG. 13, the same elements as those in FIG. 1 are represented by the same symbols without additional explanation. Since the fifth embodiment is a densitometer, the peak of transmission of interference filter 38 is at wavelength, $\lambda_3$ at which the light absorption by the pigment does not occur, while the peak of transmission of interference filter 39 is at a wavelength, $\lambda_4$ at which the light absorption by the pigment effectively occurs. Therefore, the output voltages $E_{10}$ and $E_{11}$ of the pair of photoelectric devices 5 and 6 are as follows, respectively, which are substantially similar to equations (1) and (2):

$$E_{10} = K_1 I_{03} F_{T3} D_3 \, e^{-g_3 \sqrt{\beta_3} \, (d+\Delta d)} \quad (22a)$$

$$E_{11} = K_2 I_{04} F_{T4} D_4 \, e^{-g_4 \sqrt{\beta_2} \, (d+\Delta d)} \quad (22b)$$

wherein: $I_{03}$ and $I_{04}$ represent the intensities of source light at wavelengths $\lambda_3$ and $\lambda_4$, respectively; $F_{T3}$ and $F_{T4}$ represent the light absorption coefficients of materials other than the arterial blood at wavelengths $\lambda_3$ and $\lambda_4$, respectively; $D_3$ and $D_4$ represents a pair of constants depending on the scattering coefficient and the absorption coefficient of the arterial blood at wavelengths $\lambda_3$ and $\lambda_4$, respectively; $g_3$ and $g_4$ represent a pair of constants depending on the scattering coefficients of the arterial blood at wavelengths $\lambda_3$ and $\lambda_4$ and the total density of the hemoglobin and the hemoglobin oxide, respectively; and $\beta_3$ and $\beta_4$ represent the light absorption coefficient of the arterial blood at wavelengths $\lambda_3$ and $\lambda_4$.

The output voltages, $E_{12}$ and $E_{13}$ of the pair of first calculation circuits 7 and 8 are as follows as in the first embodient:

$$E_{12} = g_3 \sqrt{\beta_3} \, d \quad (23)$$

$$E_{13} = g_4 \sqrt{\beta_4} \, d \quad (24)$$

Further, the output voltage, $E_{14}$ of dividing circuit 11 is as follows:

$$E_{14} = \left(\frac{g_4}{g_3}\right)^2 \frac{\beta_4}{\beta_3} = \left(\frac{E_{13}}{E_{12}}\right)^2 \quad (25)$$

Here, it should be noted that the light absorption coefficients, $\beta_3$ and $\beta_4$ are generally defined by the following equations, provided that $\mu_1$ and $\mu_2$ represent the light absorption coefficients of the total of hemoglobin and hemoglobin oxide at wavelengths $\lambda_3$ and $\lambda_4$, respectively, C' represents the density of the pigment in the blood and $\mu_2'$ represent the light absorption coefficient of the pigment at wavelength $\lambda_4$:

$$\beta_3 = C\mu_1 \quad (26)$$

$$\beta_4 = C\mu_2 + C'\mu_2' \quad (27)$$

From equations (25) to (27), the following equation results:

$$\left(\frac{E_{13}}{E_{12}}\right)^2 = \left(\frac{g_4}{g_3}\right)^2 \left(\frac{\mu_2}{\mu_1} + \frac{C'}{C} \cdot \frac{\mu_2'}{\mu_1}\right) \quad (28)$$

Therefore, $$C' = \left(\frac{g_3}{g_4}\right)^2 \cdot \frac{\mu_1}{\mu_2'} \cdot C \left(\frac{E_{13}}{E_{12}}\right)^2 - \frac{\mu_2}{\mu_2'} C \quad (29)$$

The constants $A_4$ and $B_3$ in circuit 40 of FIG. 13 are defined as follows:

$$\left(\frac{g_3}{g_4}\right)^2 \cdot \frac{\mu_1}{\mu_2'} \cdot C = A_4 \quad (30)$$

$$-\frac{\mu_2}{\mu_2'} C = B_3 \quad (31)$$

The equation (29) can be summarized as follows:

$$C' = A_4 \left(\frac{E_{13}}{E_{12}}\right)^2 + B_3 \quad (32)$$

Circuit 40 in FIG. 13 carries out a calculation in accordance with the linear function (32) with respect to $(E_{13}/E_{12})^2$, which is the output of dividing circuit 11. As the value for C in equations (30) and (31), an average value of various healthy men is applicable, or alternatively a personal value may be previously measured and applied, although the value for C does not particularly depend on the individual persons, but is rather common. Thus, the fifth embodiment in FIG. 13 functions as a densitometer for a desired pigment in the blood.

Clinical experiments in utilizing the device according to the present invention have shown that the measurement result is quite accurate throughout a wide range of variation in the oxygen saturation or the density of desired pigment in the blood in comparison with the prior art noninvasive oximeter using a pair of wavelengths.

While the above embodiments have been disclosed as the best modes presently contemplated by the inventor, it should be realized that these examples should not be interpreted as limiting, because artisans skilled in the field, once given the present teachings can vary from these specific embodiments. Accordingly, the scope of the present invention should be determined solely from the following claims.

What is claimed is:

1. A noninvasive device for photoelectrically measuring a property of arterial blood in living tissue comprising:
   means for generating a source light and causing said light to enter into living tissue, such that the light generating means remains outside the living tissue and only the generated light passes into the living tissue;
   means for photoelectrically measuring the intensity of the source light emerging from the living tissue after contact with the arterial blood therein, at a pair of separate wavelengths, to produce a pair of electrical signals, respectively, each signal including an alternating-current component and a direct-current component;
   means for calculating information from said pair of electric signals representative of the relative amplitude of the alternating-current component compared to the direct-current component for each of the measured wavelengths and for producing first and second calculated outputs, respectively, each output representing a respective said relative amplitude;
   means for obtaining a final output signal according to a function containing the square of a ratio between the first and second calculated outputs and containing no terms of first order in said ratio; and
   means for indicating the property of the arterial blood in response to the final output.

2. The invention of claim 1, wherein said obtaining means includes means for approximating the linear function of the square of the ratio as a joint combination of a plurality of linear functions of the ratio.

3. The invention of claim 1, wherein said approximating means includes means for selecting one of the plurality of linear functions for use in approximating, the one selected being dependent upon the level of the ratio.

4. The invention of claim 1, wherein the obtaining means includes a microprocessor and an associated digital memory circuit.

5. The invention of claim 1, wherein the obtaining means includes means for previously storing various values for the final output signal in relation to a variety of possible combinations of values for the first and second calculated outputs, and means for searching a specific value for the final output signal in accordance with a specific combination of values for the first and second calculated outputs actually obtained by the calculating means.

6. A noninvasive device for photoelectrically measuring a property of arterial blood in living tissue comprising:
   means for providing a source light to enter into living tissue from the outside thereof;
   means for photoelectrically measuring the intensity of the source light emerging from the living tissue after contact with the arterial blood contained therein, at a predetermined pair of wavelengths within the source light, and for producing a pair of electrical signals respectively representing the intensity at each wavelength;
   means for generating information representative of the relative variation in amplitude of each of the electric signals with respect to a reference level;
   means for obtaining a final output signal according to a function containing the square of a ratio between the information from said generating means for the first of the pair or wavelengths and that for the second pair thereof and containing no terms of first order in said ratio; and
   means for indicating the property of the arterial blood in response to the final output signal.

7. The invention of claim 6, wherein said obtaining means includes means for approximating the linear function of the square of the ratio as a joint combination of a plurality of linear functions of the ratio.

8. The invention of claim 6, wherein said approximating means includes means for selecting one of the plurality of linear functions for use in approximating, the one selected being dependent upon the level of the ratio.

9. The invention of claim 6, wherein the obtaining means includes a microprocessor and an associated digital memory circuit.

10. The invention of claim 6, wherein the obtaining means includes means for previously storing various values for the final output signal in relation to a variety of possible combinations of values for the first and second calculated outputs, and means for searching a specific value for the final output signal in accordance with a specific combination of values for the first and second calculated outputs actually obtained by the calculating means.

11. A noninvasive device for photoelectrically measuring a property of arterial blood in living tissue comprising:
   means for generating a source light and causing said light to enter into living tissue, such that the light generating means remains outside the living tissue and only the generated light passes into the living tissue;
   means for photoelectrically measuring the intensity of the source light emerging from the living tissue after contact with the arterial blood therein, at a pair of separate wavelengths, to produce a pair of electrical signals, respectively, each signal including an alternating-current component and a direct-current component;
   means for calculating information from said pair of electric signals representative of the relative amplitude of the alternating-current component compared to the direct-current component for each of the measured wavelengths and for producing first and second calculated outputs, respectively, each output representing a respective said relative amplitude;
   means for obtaining a final output signal according to a function having a variable which is the ratio between the first and second calculated outputs and which contains at least one second order term of said variable and no first order terms in said variable; and
   means for indicating the property of the arterial blood in response to the final output.

12. The invention of claim 11, wherein said obtaining means includes means for approximating the linear function of the square of the ratio as a joint combination of a plurality of linear functions of the ratio.

13. The invention of claim 11, wherein said approximating means includes means for selecting one of the plurality of linear functions for use in approximating, the one selected being dependent upon the level of the ratio.

14. The invention of claim 11, wherein the obtaining means includes a microprocessor and an associated digital memory circuit.

15. The invention of claim 11, wherein the obtaining means includes means for previously storing various values for the final output signal in relation to a variety of possible combinations of values for the first and second calculated outputs, and means for searching a specific value for the final output signal in accordance with a specific combination of values for the first and second calculated outputs actually obtained by the calculating means.

16. A noninvasive device for photoelectrically measuring a property of arterial blood in living tissue comprising:
 means for providing a source light to enter into living tissue from the outside thereof;
 means for photoelectrically measuring the intensity of the source light emerging from the living tissue after contact with the arterial blood contained therein, at a predetermined pair of wavelengths within the source light, and for producing a pair of electrical signals respectively representing the intensity at each wavelength;
 means for generating information representative of the relative variation in amplitude of each of the electric signals with respect to a reference level;
 means for obtaining a final output signal according to a function having a variable which is the ratio between the information from said generating means for the first of the pair of wavelengths and that for the second of the pair thereof and which contains at least one second order term of said variable and no first order terms of said variable; and
 means for indicating the property of the arterial blood in response to the final output signal.

17. The invention of claim 16, wherein said obtaining means includes means for approximating the linear function of the square of the ratio as a joint combination of a plurality of linear functions of the ratio.

18. The invention of claim 16, wherein said approximating means includes means for selecting one of the plurality of linear functions for use in approximating, the one selected being dependent upon the level of the ratio.

19. The invention of claim 16, wherein the obtaining means includes a microprocessor and an associated digital memory circuit.

20. The invention of claim 16, wherein the obtaining means includes means for previously storing various values for the final output signals in relation to a variety of possible combinations of values for the first and second calculated outputs, and means for searching a specific value for the final output signal in accordance with a specific combination of values for the first and second calculated outputs actually obtained by the calculating means.

* * * * *